(12) United States Patent
Moon et al.

(10) Patent No.: US 10,296,779 B2
(45) Date of Patent: May 21, 2019

(54) METHOD OF MEASURING RED BLOOD CELL MEMBRANE FLUCTUATIONS BASED ON DYNAMIC CELL PARAMETERS AND DIGITAL HOLOGRAPHIC MICROSCOPE USED THEREFOR

(71) Applicant: Industry-Academic Cooperation Foundation, Chosun University, Gwangju (KR)

(72) Inventors: Inkyu Moon, Gwangju (KR); Keyvan Jaferzadeh, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 0 days.

(21) Appl. No.: 15/622,081

(22) Filed: Jun. 14, 2017

(65) Prior Publication Data

US 2017/0356845 A1     Dec. 14, 2017

(30) Foreign Application Priority Data

Jun. 14, 2016  (KR) .................. 10-2016-0073986

(51) Int. Cl.
| | |
|---|---|
| *G03H 1/00* | (2006.01) |
| *G03H 1/04* | (2006.01) |
| *G06K 9/00* | (2006.01) |
| *G01N 15/00* | (2006.01) |
| *G01N 15/14* | (2006.01) |

(52) U.S. Cl.
CPC ..... *G06K 9/00134* (2013.01); *G01N 15/1434* (2013.01); *G01N 15/1475* (2013.01); *G03H 1/0443* (2013.01); *G01N 2015/0073* (2013.01); *G01N 2015/1445* (2013.01); *G01N 2015/1454* (2013.01); *G01N 2015/1497* (2013.01); *G03H 2001/0033* (2013.01); *G03H 2001/0447* (2013.01); *G03H 2001/0452* (2013.01); *G03H 2210/30* (2013.01)

(58) Field of Classification Search
None
See application file for complete search history.

(56) References Cited

FOREIGN PATENT DOCUMENTS

| JP | 2000-002839 | 1/2000 |
|---|---|---|
| KR | 10-2005-0035542 | 4/2005 |

OTHER PUBLICATIONS

Rappaz, Benjamin, et al. "Spatial analysis of erythrocyte membrane fluctuations by digital holographic microscopy." Blood Cells, Molecules, and Diseases 42.3 (2009): 228-232.*

(Continued)

*Primary Examiner* — Shawn Decenzo
(74) *Attorney, Agent, or Firm* — Eric Kelly

(57) ABSTRACT

Disclosed is a method of measuring red blood cell membrane fluctuations based on dynamic cell parameters using a digital holographic microscope; the method including a step of modeling the three-dimensional images of red blood cells to be measured, and a step of measuring red blood cell membrane fluctuations based on the three-dimensional images. According to this method, since the three-dimensional images of red blood cells to be measured are modeled and red blood cell membrane fluctuations are measured based on the three-dimensional images, red blood cell membrane fluctuations can be measured more easily.

11 Claims, 8 Drawing Sheets
(6 of 8 Drawing Sheet(s) Filed in Color)

(56) References Cited

OTHER PUBLICATIONS

Faliu Yi, "Quantitative Analysis of Three-dimensional Morphology and Biophysical Cell Parameters of Live Cells using Digital Holographic Imaging", Aug. 25, 2015, Chosun University, KR.

* cited by examiner

METHOD OF MEASURING RED BLOOD CELL MEMBRANE FLUCTUATIONS BASED ON DYNAMIC CELL PARAMETERS AND DIGITAL HOLOGRAPHIC MICROSCOPE USED THEREFOR

PRIORITY NOTICE AND CROSS-REFERENCE TO RELATED APPLICATION

The present application claims priority under 35 U.S.C. § 119 to Korean patent application, number 2016-0073986 filed on Jun. 14, 2017, the disclosure of which is incorporated herein by reference in its entirety.

TECHNICAL FIELD OF THE INVENTION

The present disclosure relates to a method of measuring red blood cell membrane fluctuations based on dynamic cell parameters using a digital holographic microscope; and more particularly, to a method of measuring red blood cell membrane fluctuations based on dynamic cell parameters, wherein three-dimensional images of a red blood cell to be measured are modeled and the morphological parameters of the red blood cell are measured based on the three-dimensional image, and to a digital holographic microscope used therefor.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Red blood cells are made up of water and proteins such as hemoglobin, and cell membranes thereof consist mainly of water, lipids, proteins, and carbohydrates. Mature red blood cells are the most common type of blood cells involved in blood circulation. As for the morphology of a red blood cell, a red blood cell (often referred to as a discocyte) has a flexible membrane of a double-sided concave shape that is optimal for maximum deformation, maximum surface exposure at a given volume, and rapid morphological changes during passage through small capillaries in microcirculation.

In particular, since the internal structure of a red blood cell is not complicated, the double-sided concave shape of a red blood cell is regarded as a result of minimizing the free energy of the cell membrane under the above-mentioned area and volume limitations. Red blood cells must adapt to capillaries having a relatively wide range of sizes in blood vessels, but red blood cells must be able to deform while maintaining cell integrity and functions thereof. Such deformation is possible because red blood cells do not have a three-dimensional cytoskeleton. On the other hand, the morphology and mechanical integrity of red blood cells can be maintained, at the time of the deformation, by two-dimensional triangular lattices formed by flexible spectrin tetramers linked by actin oligomers. Since the lateral length (70 to 80 nm) of actin is shorter than the contour length (about 200 nm) of a spectrin tetramer, spectrin is considered to act as a major contributor to the bending modulus or curvature of red blood cells.

Conventionally, biochemical methods were applied to measure parameters required for measuring the condition of red blood cells, and thus it was difficult to measure red blood cell membrane fluctuations.

SUMMARY OF THE INVENTION

Therefore, the present disclosure has been made in view of the above problems, and it is an objective of the present disclosure to provide a method of measuring red blood cell membrane fluctuations based on dynamic cell parameters, wherein three-dimensional images of red blood cells to be measured are modeled and red blood cell membrane fluctuations are measured based on the three-dimensional images, and a digital holographic microscope is used therefor.

In accordance with the present disclosure, the above and other objectives can be accomplished by the provision of a method of measuring red blood cell membrane fluctuations based on dynamic cell parameters, the method including a step of modeling three-dimensional images of a red blood cell to be measured, and a step of measuring red blood cell membrane fluctuations based on the three-dimensional image.

The step of modeling may be performed by obtaining three-dimensional images from the red blood cell to be measured using a digital holographic microscope.

The step of modeling may include a step of generating an optical interference signal through an object beam passing through the red blood cell and a reference beam emitted from a light source unit and producing a holographic image by capturing the optical interference signal using an image capturing unit, and a step of modeling three-dimensional images of the red blood cell based on the holographic image.

The step of generating may be performed by transmitting the object beam from the lower side to the upper side of the red blood cell.

The step of generating is preferably performed by transmitting the object beam in a direction crossing the radial direction of the red blood cell to obtain a holographic image of a concave portion formed at the center of the disc-shaped red blood cell having a predetermined radius.

In the step of generating, a plurality of three-dimensional images may be produced by photographing the red blood cell at predetermined time intervals, and the step of measuring may be performed by sequentially superimposing the three-dimensional images on each other according to photographing time and calculating red blood cell membrane fluctuations.

The step of measuring may include a step of dividing the three-dimensional images into a dimple range corresponding to a dimple portion recessed in the center of the red blood cell, and an outer ring range corresponding to an outer ring portion, excluding the dimple portion, present in the surface of the red blood cell in which the dimple portion is formed; and a step of calculating the fluctuation rate of the whole cell membrane of the red blood cell, the fluctuation rate of the dimple range and the fluctuation rate of the outer ring range, respectively, by superimposing the three-dimensional images on each other.

In the step of measuring, a red blood cell membrane fluctuation ($CMF_{cell}(x,y)$) may be calculated by Equation 1 below:

$$CMF_{cell}(x, y) = \sqrt{(std(h_{cell} + h_{background})(x, y))^2 - (std(h_{background}))^2}$$ Equation 1 wherein $std(h_{cell}+h_{background})(x,y)$ indicates the temporal deviation of a part corresponding to the red blood cell and a background in the three-dimensional image, and $std(h_{background})$ indicates an average of the temporal deviation of the background except the part corresponding to the red blood cell in the three-dimensional image.

In addition, the method according to the present disclosure may further comprise a step of estimating a state of the red blood cell based on red blood cell membrane fluctuations measured in the step of measuring.

In addition, in the step of modeling, a plurality of red blood cell samples may each be modeled as three-dimensional images, in the step of measuring, a red blood cell membrane fluctuation with respect to each of the red blood cell samples may be measured based on the three-dimensional images of the red blood cell samples; and, in the step of estimating, the elapsed retention time of each of the red blood cell samples after blood collection may be estimated based on the cell membrane fluctuation rates of the red blood cell samples.

In accordance with an aspect of the present disclosure, the above and other objectives can be accomplished by the provision of a digital holographic microscope including a light source unit configured to generate an object beam and a reference beam, wherein the radiated object beam is transmitted through a red blood cell to be measured; a beam splitter configured to receive the object beam transmitted through the red blood cell and the reference beam and generate an optical interference signal; and an image capturing unit configured to photograph the optical interference signal generated from the beam splitter, wherein the light source unit transmits the object beam in a direction crossing the radial direction of the red blood cell to acquire the images of a concave portion formed at the center of the disc-shaped red blood cell having a predetermined radius.

In addition, the digital holographic microscope according to the present disclosure may additionally include a setting plate, which is made of a light transmissive material through which the object beam is transmitted, and on which the red blood cell is set so that the concave portion is located on the upper side. Preferably, the object beam is radiated from the light source unit so that the object beam is transmitted from the lower side to the upper side of the setting plate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present disclosure will become more apparent to those of ordinary skill in the art by describing embodiments thereof in detail with reference to the accompanying drawings, in which.

Figure 1:
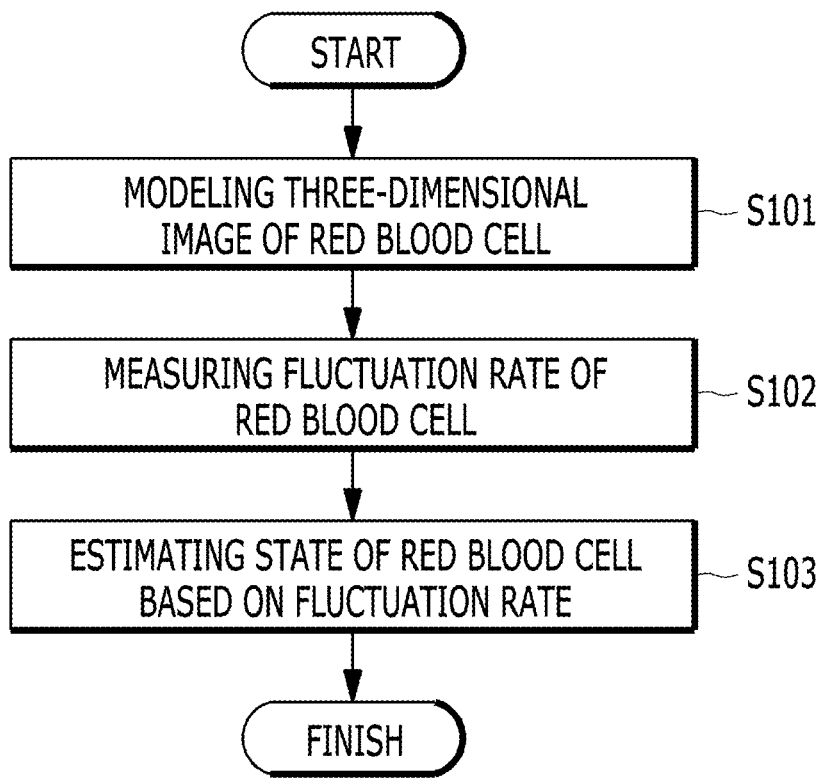
FIG. 1 is a flowchart illustrating the method of measuring red blood cell membrane fluctuations based on dynamic cell parameters according to the present disclosure.

REFERENCE NUMERAL SCHEDULE 11 object beam 11
12 reference beam 12
100 digital holographic microscope 100
110 setting plate 110
111 transmitting plates 111
112 spacing members 112
120 beam splitter 120
125 objective lens 125
130 image capturing unit 130
S101 modeling step S101
S102 fluctuation rate measurement step S102
S103 estimation step S103

DETAILED DESCRIPTION OF EMBODIMENTS OF THE INVENTION

Hereinafter, according to the embodiments of the present disclosure, a method of measuring red blood cell membrane fluctuations based on dynamic cell parameters and a digital holographic microscope used therefor is described in detail with reference to the accompanying drawings. Since the present disclosure may be applied with various modifications and may have various embodiments, some embodiments and drawings of the present disclosure are explained and discussed explicitly herein. However, such embodiments and drawings are not intended to limit the embodiments of the present disclosure to particular modes of practice, and all changes, equivalents, and substitutes that do not depart from the spirit and technical scope of the present disclosure should be understood as being encompassed in the present disclosure. Like reference numerals refer to like elements in describing each drawing. In the accompanying drawings, the dimensions of the structures are enlarged, compared to an actual view, for clarity of the present disclosure.

The terms such as "first" and "second" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the teachings of the present disclosure.

The terms used in the present specification are used for explaining specific embodiments, not limiting the present inventive concepts. Thus, the expression of singularity in the present specification includes the expression of plurality unless clearly specified otherwise in context. Also, the terms such as "include" or "comprise" are used to specify stated characteristics, numbers, steps, operations, constituent elements, or a combination thereof, but should not be construed to exclude the existence of or a possibility of addition of one or more other characteristics, numbers, steps, operations, constituent elements, and/or combinations thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In FIG. 1, a flowchart illustrating the method of measuring red blood cell membrane fluctuations based on dynamic cell parameters according to the present disclosure is shown.

Referring to this flowchart in FIG. 1, the method of measuring red blood cell membrane fluctuations based on dynamic cell parameters includes a modeling step (S101), a fluctuation rate measurement step (S102), and an estimation step (S103).

Figure 2:
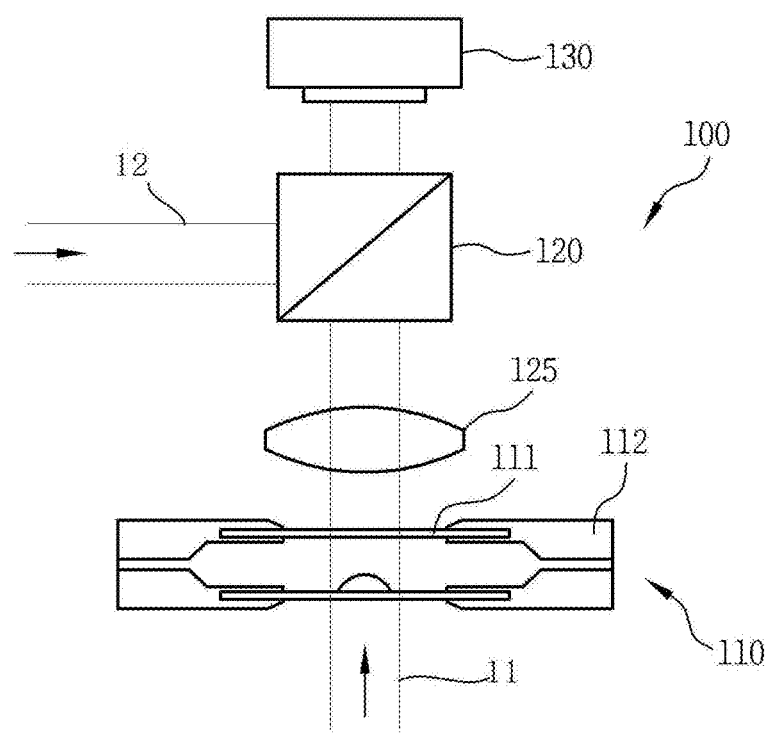
FIG. 2 is a conceptual diagram illustrating a digital holographic microscope used in the method of measuring red blood cell membrane fluctuations based on dynamic cell parameters according to the present disclosure.

In the modeling step (S101), the three-dimensional images of red blood cells to be measured are modeled. The modeling step (S101) is a step of acquiring three-dimensional images from red blood cells to be measured using a digital holographic microscope (such as digital holographic microscope 100 shown in FIG. 2), and includes a hologram production step and a three-dimensional image production step.

Digital holographic microscope 100 is described in detail as follows. The digital holographic microscope 100 according to the present disclosure includes a setting plate 110 on which a red blood cell to be measured is set, a light source unit for generating an object beam 11 and a reference beam 12, wherein the object beam 11 is radiated from the light source unit so that the object beam 11 is transmitted through the red blood cell to be measured, a beam splitter 120 for receiving the object beam 11 transmitted through the red blood cell and the reference beam 12 and generating an optical interference signal, and an image capturing unit 130 for photographing the optical interference signal generated from the beam splitter 120. See e.g., FIG. 2.

The setting plate 110 is made of a material through which the object beam 11 can be transmitted and includes a plurality of transmitting plates 111 supported by spacing members 112 so as to be spaced apart from each other in a vertical direction. Between the transmitting plates 111, there are provided seating spaces in which blood containing red blood cells is seated. A concave portion is formed at the center of the disc-shaped red blood cell having a predetermined radius, and the red blood cell is preferably set so that the concave portion is located on the upper side between the transmitting plates 111. See e.g., FIG. 2.

Although not shown in the drawing, the light source unit includes a first light source installed below the setting plate 110 and irradiating the object beam 11 toward the setting plate 110, and a second light source for irradiating the reference beam 12 onto the optical path of the object beam 11 transmitted through the setting plate 110. The first and second light sources correspond to the object beam 11 and the reference beam 12, respectively, and are preferably lasers having a wavelength of 682 nm. See e.g., FIG. 2.

When irradiating light, the light source unit preferably transmits the object beam 11 in a direction crossing the radial direction of the red blood cell to acquire a holographic image of a concave portion formed at the center of the red blood cell.

The beam splitter 120 is installed at a position where the optical path of the object beam 11 and the optical path of the reference beam 12 intersect and generates an optical interference signal from the object beam 11 transmitted through the red blood cell and the reference beam 12. The beam splitter 120 generating an optical interference signal between the object beam 11 and the reference beam 12 is a beam splitter used in a conventional digital holographic microscope, and thus a detailed description thereof is omitted. See e.g., FIG. 2.

An objective lens 125 may be provided on the optical path of the object beam 11 between the beam splitter 120 and the setting plate 110. It may be preferable that the magnification of the objective lens 125 is 40× and the field of view is 150 μm. See e.g., FIG. 2.

The image capturing unit 130 to which a CCD (charge coupled device) camera or the like, is applied and is installed on the upper side of the beam splitter 120, and captures an optical interference signal generated by the beam splitter 120. See e.g., FIG. 2.

In the hologram production step (e.g., a sub-step of the modeling step (S101)), an optical interference signal is generated through the object beam 11 transmitted through the red blood cell and the reference beam 12 emitted from the light source unit, and the optical interference signal is captured by the image capturing unit 130 to produce a holographic image. The light source unit is operated to generate the object beam 11 and the reference beam 12, and an optical interference signal generated by the beam splitter 120 is captured to acquire a holographic image. At this time, it may be preferable that experimenters (e.g., users of the method disclosed herein) set red blood cells on the setting plate 110 so that concave portions of such red blood cells are positioned on the upper side of the setting place 110, or only red blood cells with the concave portions facing upward among captured images are selected and measured.

Figure 3:
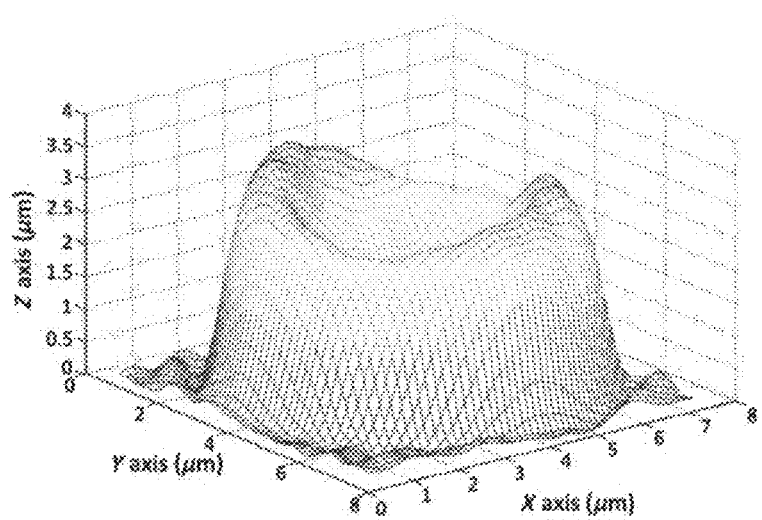
FIG. 3 shows the three-dimensional image of a red blood cell, which is modeled by the method of measuring red blood cell membrane fluctuations based on dynamic cell parameters according to the present disclosure.

A three-dimensional image production step (e.g., another sub-step of the modeling step (S101)) is a step of modeling the three-dimensional image of the red blood cell based on the holographic image prepared in the hologram production step. A three-dimensional image produced by modeling based on the holographic image of a red blood cell sample is shown in FIG. 3.

In the modeling step (S101), it is preferable that a plurality of three-dimensional images are generated by photographing the red blood cell(s) at predetermined time intervals. In some embodiments, such predetermined time intervals for photographing red blood cells may be very short, such as on the order of microseconds.

In the fluctuation rate measurement step (S102), red blood cell membrane fluctuations are measured based on three-dimensional images obtained from the modeling step (S101). A red blood cell membrane fluctuation ($CMF_{cell}(x, y)$) is calculated by Equation 1 below:

$$CMF_{cell}(x, y) = \sqrt{(std(h_{cell} + h_{background})(x, y))^2 - (std(h_{background}))^2} \qquad \text{Equation 1}$$

wherein $std(h_{cell}+h_{background})(x,y)$ indicates the temporal deviation of a part corresponding to the red blood cell and a background in the three-dimensional image, and $std(h_{background})$ indicates an average of the temporal deviation of the background except the part corresponding to the red blood cell in the three-dimensional image.

Figure 4:
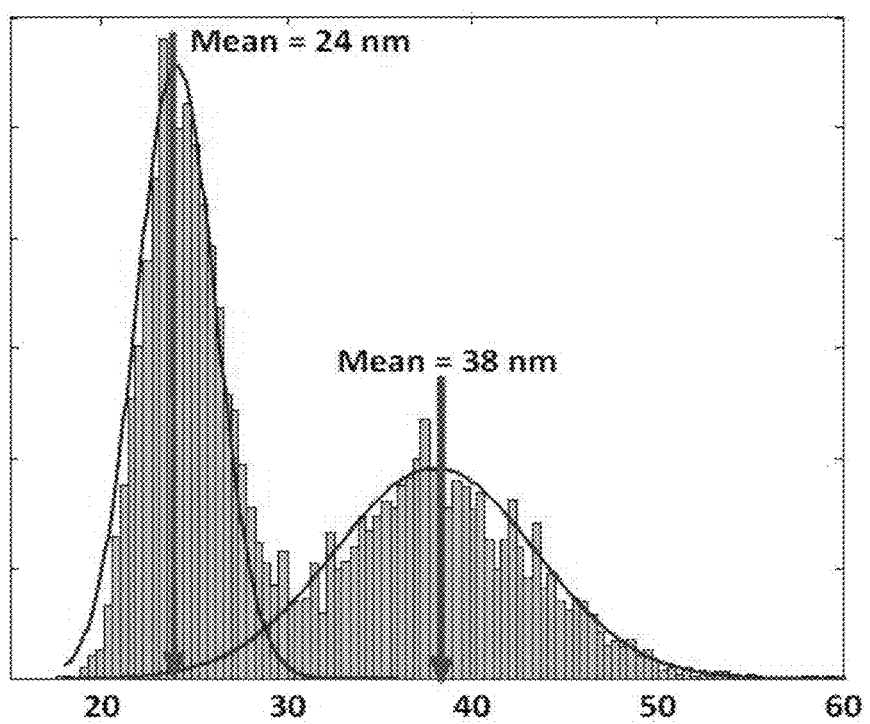
FIG. 4 is a graph showing the distribution of the temporal deviations of parts corresponding to red blood cells and the temporal deviations of backgrounds in three-dimensional images modeled by the method of measuring red blood cell membrane fluctuations based on dynamic cell parameters according to the present disclosure.

FIG. 4 includes a graph showing the distribution of the temporal deviations of parts corresponding to red blood cells and the temporal deviations of backgrounds in three-dimensional images. Here, a left distribution relates to the temporal deviation of a background, and the right distribution relates to the temporal deviation of the cell membrane and noise.

In the three-dimensional image of the red blood cell, the standard deviation of a dimple range corresponding to a dimple portion recessed in the center of a red blood cell is 4.237 nm, the standard deviation of an outer ring range corresponding to an outer ring portion, excluding the dimple portion, present in the surface of the red blood cell in which the dimple portion is formed, is 29.25 nm, and the standard deviation of a background is 17.85 nm.

To increase the accuracy with respect to red blood cell membrane fluctuations, experimenters may either remove the noise of the three-dimensional images by imparting temporal summation to the three-dimensional images, or use a median filter with a pixel size of 5×5.

In addition, when the transverse displacement of red blood cells occurs during the examination, the transverse displacement may be invalidated by using image software and the StackReg plugin or the like.

In addition, since the cell boundaries of red blood cells and the periphery of the center of red blood cells have high slopes, the thickness changes may occur when an object beam 11 is transmitted. Therefore, to prevent such a phenomenon, it may be preferable to evaluate cell fluctuations in a direction perpendicular to the red blood cell membrane.

The fluctuation rate measurement step (S102) may include a dividing step and a calculating step.

Figure 5:
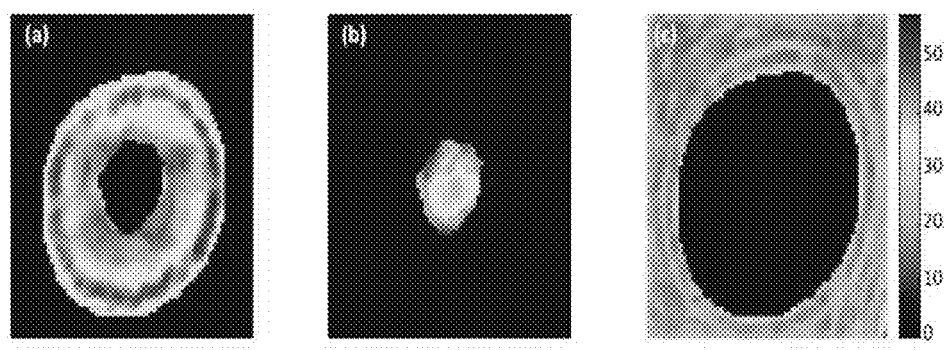
FIG. 5 shows the deviation maps of an outer ring range, a dimple range, and a background excluding the outer ring and dimple ranges in the three-dimensional image.

In the dividing step, the three-dimensional image is divided into a dimple range corresponding to a dimple portion recessed in the center of the red blood cell and an outer ring range corresponding to an outer ring portion, excluding the dimple portion, present in the surface of the red blood cell in which the dimple portion is formed. At this time, each range is partitioned in the three-dimensional image using binary masks. The binary masks are generated using simple thresholds and the binary operators of erosion. In FIG. 5, the deviation maps of an outer ring range, a dimple range, and a background excluding the outer ring and dimple ranges are shown. In the deviation maps, (a) of FIG. 5 is a deviation map with respect to the outer ring range; (b) of FIG. 5 is a deviation map with respect to the dimple range; and (c) of FIG. 5 is a deviation map with respect to the background excluding the outer ring and dimple ranges.

As described above, based on the measured red blood cell membrane fluctuations, the state of red blood cells, that is, elapsed retention time or freshness after blood sampling, may be estimated. That is, when a storage period is long or freshness is low, red blood cell membrane fluctuations are decreased, which may be estimated by comparing red blood cell membrane fluctuations and the morphological and biochemical parameters of red blood cells.

The following is a detailed description of measurements taken to determine the relationship between the fluctuation rate of red blood cell membranes and the morphological parameters of red blood cells.

First, the morphological parameters of red blood cells to be compared with red blood cell membrane fluctuations include: red blood cell volume; the projected surface area (PSA) of red blood cells; and the sphericity coefficient (k) of red blood cells.

The red blood cell volume (V) is calculated by Equation 2 below:

$$V \cong p^2 \sum_{i=1}^{m} \sum_{j=1}^{l} h(i, j) \qquad \text{Equation 2}$$

wherein, p indicates a pixel size in a three-dimensional image, m and l indicate the width and height of a red blood cell area in the three-dimensional image, respectively, and $h(i, j)$ indicates the thickness value of the three-dimensional image at the pixel $(i, j)$.

In addition, the projected surface area (PSA) of red blood cells is calculated by Equation 3 below:

$$PSA = Np^2 \qquad \text{Equation 3}$$

wherein, p indicates a pixel size in a three-dimensional image, N indicates the total number of pixels in a red blood cell range of the three-dimensional image (N=m×l). The decrease in the projected surface area of red blood cells (PSA) is proportional to the increase in the storage period after red blood cell collection.

Next, the sphericity coefficient (k) of red blood cells is calculated by Equation 4 below:

$$k = \frac{d_c}{d_r} \qquad \text{Equation 4}$$

wherein, $d_c$ indicates the thickness value of the three-dimensional image at a position corresponding to the center of the red blood cell, $d_r$ indicates the thickness value of the three-dimensional image at a position corresponding to a half of the radius of the red blood cell in a radial direction from the center of the red blood cell. That is, the sphericity coefficient (k) of red blood cells is preferably a ratio of the thickness value of the three-dimensional image at a position corresponding to the center of the red blood cell to the thickness value of the three-dimensional image at a position corresponding to a half of the radius of the red blood cell in a radial direction from the center of the red blood cell.

The sphericity coefficient of the red blood cell indicates the shape of the center of red blood cell. When the sphericity coefficient is smaller than 1, it indicates that the concave portion is formed in the center of a red blood cell. When the sphericity coefficient is 1, it indicates that the center of a red blood cell is flatly formed. When the sphericity coefficient is larger than 1, it indicates that the center of a red blood cell is convexly formed. The increase in the sphericity coefficient of the red blood cells is proportional to the increase in the storage period after red blood cell collection.

Figure 6:
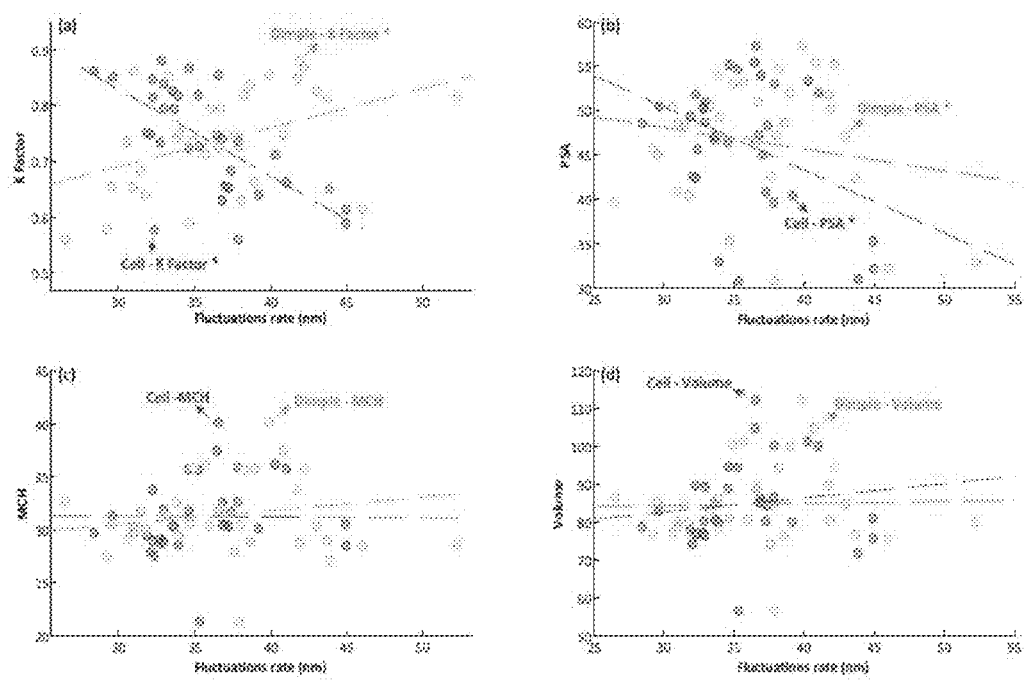
FIG. 6 and FIG. 7 include graphs showing the correlation between the fluctuations and the morphological and biochemical parameters of the whole cell membranes and the dimple ranges of red blood cells.
Figure 7:
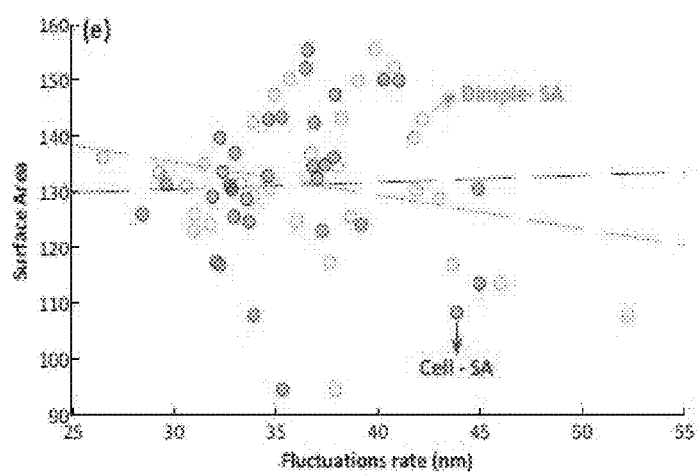

FIG. 6 and FIG. 7 include graphs showing the correlation between the fluctuation rates and the morphological and biochemical parameters of the whole cell membranes and the dimple ranges of red blood cells. Here, "Dimple" represents the dimple range of red blood cells, and "Cell" represents the whole cell membranes of red blood cells. Here, "K Factor" ((a) of FIG. 6) represents the sphericity coefficient of red blood cells; "PSA" ((b) of FIG. 6) represents the projected surface area of red blood cells; "Volume" ((d) of FIG. 6) represents the red blood cell volume; "Surface Area" (FIG. 7) represents the surface area of red blood cells; and "MCH" ((c) of FIG. 6) represents the hemoglobin content of red blood cells. The surface area of the red blood cells is calculated as a sum of the projected surface area (PSA) of red blood cells and the plane area, in a top view, of portions corresponding to red blood cells in the three-dimensional image. In addition, mean corpuscular hemoglobin (MCH) was measured by a conventional method generally used in measuring the hemoglobin content of red blood cells, and thus a detailed description of the measurement method is omitted.

(a) of FIG. 6 is a graph showing a correlation between the fluctuation rate of red blood cell membranes and the sphericity coefficient of red blood cells. The fluctuation rate of cell membranes has a negative correlation with the sphericity coefficient. That is, when the value of sphericity coefficient (k) increases, the cell membrane fluctuations decrease. This suggests that red blood cells become more rigid when red blood cells become spherical. On the other hand, the fluctuation rate of a dimple range has a positive correlation with the sphericity coefficient (k). That is, when the value of sphericity coefficient (k) in a dimple range increases, the membrane fluctuations in the dimple range increase. This is because, in the dimple range, the thickness of red blood cells having a larger value of sphericity coefficient (k) is larger than that of red blood cells having a smaller value of sphericity coefficient (k). This large thickness causes an increase in the fluctuation rate.

(b) of FIG. 6 is a graph showing the correlation between the fluctuation rate of red blood cell membranes and the projected surface area (PSA) of red blood cells. Referring to the graph, when the projected surface area of red blood cells decreases, the fluctuation rates of red blood cell membranes and a dimple range increase.

(c) of FIG. 6 is a graph showing the correlation between the hemoglobin content of red blood cells (i.e., mean corpuscular hemoglobin, MCH) and the fluctuation rate of red blood cell membranes. Referring to the graph, there is no correlation between the fluctuation rate of the whole cell membranes of red blood cells and the hemoglobin content of red blood cells, but the fluctuation rate of a dimple range increases with an increasing hemoglobin content.

(d) of FIG. 6 is a graph showing the correlation between red blood cell volume and the fluctuation rate of red blood cell membranes. Referring to the graph, the fluctuation rate of red blood cell membranes increases with an increasing red blood cell volume.

FIG. 7 is a graph showing the correlation between the fluctuation rate of red blood cell membranes and the surface area of red blood cells. Referring to the graph, the fluctuation rate of cell membranes is reduced in cells with a large surface area.

Figure 8:
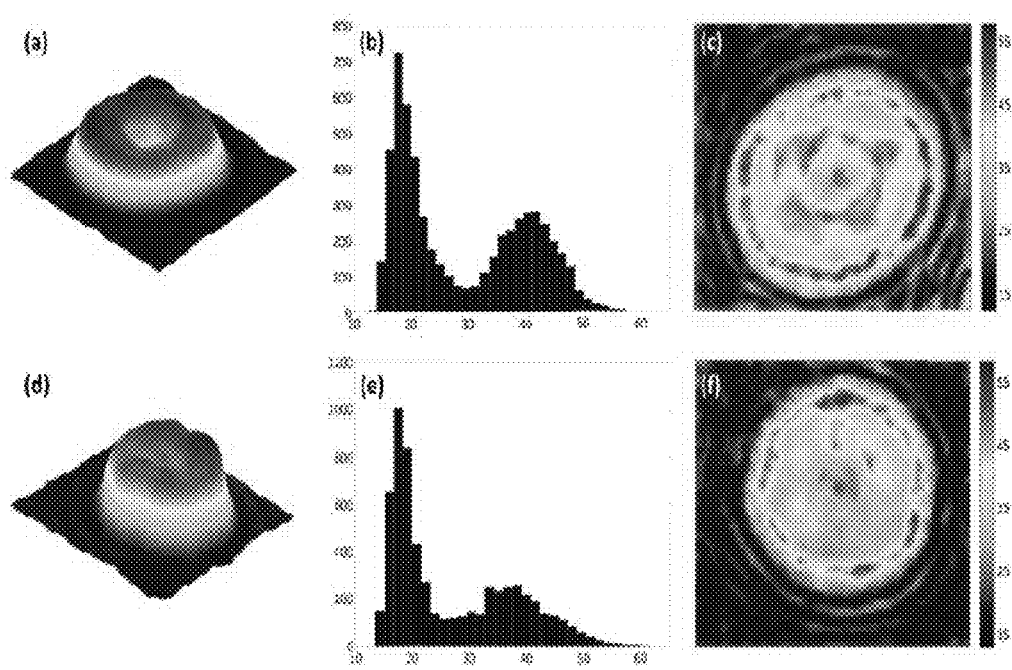
FIG. 8 is a graph showing the results of analyzing red blood cells having storage periods of 1 day and 66 days after blood collection, respectively.

FIG. 8 is a graph showing the results of analyzing red blood cells having storage periods of 1 day and 66 days after blood collection, respectively. (a) of FIG. 8 represents the three-dimensional reconstruction image of a red blood cell having a storage period of 1 day and a sphericity coefficient (k) of 0.85. (b) of FIG. 8 represents the deviation distribution of red blood cells having a storage period of 1 day. (c) of FIG. 8 represents the fluctuation map of red blood cells having a storage period of 1 day. In this case, the average fluctuation value for the whole surfaces of red blood cells having a storage period of 1 day is 34.78 nm. In addition, (d) of FIG. 8 represents the three-dimensional reconstruction image of a red blood cell having a storage period of 66 days and a sphericity coefficient (k) of 0.95. (e) of FIG. 8 represents the deviation distribution of red blood cells having a storage period of 66 days. (f) of FIG. 8 represents the fluctuation map of red blood cells having a storage period of 66 days. In this case, the average fluctuation value for the whole surfaces of red blood cells having a storage period of 66 days is 26.33 nm.

As described above, comparing red blood cell membrane fluctuations and the morphological and biochemical parameters of red blood cells, it can be seen that, when the storage period is long or the freshness is low, the fluctuation rate of red blood cell membranes decreases. That is, when the storage period of red blood cells increases or red blood cells age, the fluctuation rate of red blood cell membranes decreases.

In addition, in the estimation step (S103), the state of red blood cells, that is, retention time or freshness, is estimated based on the red blood cell membrane fluctuations measured in the fluctuation rate measurement step (S102). In this case, experimenters may collect data on red blood cell membrane fluctuations according to the storage period obtained through a plurality of previous experiments, and estimate the state of red blood cells by comparing the value of the red blood cell membrane fluctuations and the collected data.

According to the method of the present disclosure as described above, since the three-dimensional images of red blood cells to be measured are modeled and red blood cell membrane fluctuations are measured based on the three-dimensional images, red blood cell membrane fluctuations may be measured more easily.

In addition, the method of measuring red blood cell membrane fluctuations based on dynamic cell parameters according to the present disclosure may be used to estimate the retention period of red blood cell samples with different retention periods after blood collection. In the modeling step (S101), a plurality of red blood cell samples are each modeled as three-dimensional images; in the fluctuation rate measurement step (S102), a red blood cell membrane fluctuation with respect to each of the red blood cell samples is measured based on the three-dimensional images of the red blood cell samples; and in the estimation step (S103), the elapsed retention time of each of the red blood cell samples after blood collection is estimated based on the cell membrane fluctuation rates of the red blood cell samples. In this case, in the estimation step (S103), when the data on the values of cell membrane fluctuation rates depending on the storage period is sufficient, the storage time of each red blood cell sample may be more accurately estimated. However, even when the data on the values of cell membrane fluctuation rates depending on the storage period is not sufficient, it is easy to compare the storage time between red blood cell samples.

When using the method of measuring red blood cell membrane fluctuations based on dynamic cell parameters according to the present disclosure, since the three-dimensional images of red blood cells to be measured are modeled and red blood cell membrane fluctuations are measured based on the three-dimensional images, red blood cell membrane fluctuations can be measured more easily.

The description of the disclosed embodiments is provided to enable those skilled in the art to make or use the disclosure. Various modifications to these embodiments will be readily apparent to those skilled in the art, and the applicable principles defined herein may be applied to other embodiments without departing from the scope of the disclosure. Thus, the present disclosure is not limited to the embodiments described herein, and should be construed as the widest scope encompassing the principles and novel features described herein.

What is claimed is:

1. A method of measuring red blood cell membrane fluctuations based on dynamic cell parameters, the method comprising:
    modeling a plurality of three-dimensional images of a red blood cell to be measured;
    dividing the plurality of three-dimensional images into a dimple range corresponding to a dimple portion recessed in a center of the red blood cell, and an outer ring range corresponding to an outer ring portion of the red blood cell, excluding the dimple portion, present in a surface of the red blood cell in which the dimple portion is formed;
    calculating a fluctuation rate of a whole cell membrane of the red blood cell, a fluctuation rate of the dimple range, a fluctuation rate of the outer ring range, respectively, by superimposing the plurality of three-dimensional images on each other; and
    measuring red blood cell membrane fluctuations based on the fluctuation rate of the whole cell membrane, the fluctuation rate of the dimple range and the fluctuation rate of the outer ring range.

2. The method according to claim 1, wherein the modeling is performed by obtaining the plurality of three-dimensional images from the red blood cell to be measured using a digital holographic microscope.

3. The method according to claim 1, wherein the modeling comprises:
    generating an optical interference signal through an object beam passing through the red blood cell and a reference beam emitted from a light source unit and producing a holographic image by capturing the optical interference signal using an image capturing unit; and
    modeling the plurality of three-dimensional images of the red blood cell based on the holographic image.

4. The method according to claim 3, wherein the generating is performed by transmitting the object beam from a lower side to an upper side of the red blood cell.

5. The method according to claim 4, wherein, in the generating, the plurality of three-dimensional images are produced by photographing the red blood cell at predetermined time intervals, and the superimposing of the plurality of three-dimensional images on each other occurs sequentially according to photographing time and the calculating step.

6. The method according to claim 5, wherein, in the measuring, a red blood cell membrane fluctuation ($CMF_{cell}$ (x,y)) is calculated by:

$$CMF_{cell}(x, y) = \sqrt{(std(h_{cell} + h_{background}))(x, y))^2 - (std(h_{background}))^2}$$

wherein $std(h_{cell}+h_{background})(x,y)$ indicates a temporal deviation of a part corresponding to the red blood cell and a background in each of the plurality of three-dimensional images, and $std(h_{background})$ indicates an average of a temporal deviation of the background, except the part corresponding to the red blood cell in each of the plurality of three-dimensional images.

7. The method according to claim 3, wherein the generating is performed by transmitting the object beam in a direction crossing a radial direction of the red blood cell to obtain the holographic image of a concave portion formed at a center of a disc-shaped red blood cell having a predetermined radius.

8. The method according to claim 7, wherein, in the generating, the plurality of three-dimensional images are produced by photographing the red blood cell at predetermined time intervals, and the superimposing of the plurality of three-dimensional images on each other occurs sequentially according to photographing time and the calculating step.

9. The method according to claim 8, wherein, in the measuring, a red blood cell membrane fluctuation ($CMF_{cell}$ (x,y)) is calculated by:

$$CMF_{cell}(x, y) = \sqrt{(std(h_{cell} + h_{background}))(x, y))^2 - (std(h_{background}))^2}$$

wherein $std(h_{cell}+h_{background})(x,y)$ indicates a temporal deviation of a part corresponding to the red blood cell and a background in each of the plurality of three-dimensional images, and $std(h_{background})$ indicates an average of a temporal deviation of the background, except the part corresponding to the red blood cell in each of the plurality of three-dimensional images.

10. The method according to claim 1, the method further comprising estimating a state of the red blood cell based on red blood cell membrane fluctuations measured in the measuring.

11. The method according to claim 10, wherein, in the modeling, a plurality of red blood cell samples are each modeled as the plurality of three-dimensional images; in the measuring, a red blood cell membrane fluctuation with respect to each of the red blood cell samples is measured based on the plurality of three-dimensional images of the red blood cell samples; and, in the estimating, elapsed retention time of each of the red blood cell samples after blood collection is estimated based on the cell membrane fluctuation rates of the red blood cell samples.

* * * * *